United States Patent [19]

Carpentier

[11] Patent Number: 5,135,539
[45] Date of Patent: Aug. 4, 1992

[54] QUICK-CONNECT, TOTALLY IMPLANTABLE CARDIAC PROSTHESIS WITH FLOATING MEMBRANES AND REMOVABLE SENSITIVE ELEMENTS

[75] Inventor: Alain Carpentier, Paris, France

[73] Assignee: Etablissement Public: Universite Pierre et Marie Curie, Paris, France

[21] Appl. No.: 295,761

[22] Filed: Jan. 11, 1989

[30] Foreign Application Priority Data

Jan. 14, 1988 [FR] France ............................ 88 00381

[51] Int. Cl.$^5$ .................... A61M 1/10; A61N 1/362
[52] U.S. Cl. ............................................ 623/3; 600/16
[58] Field of Search ...................... 623/3; 600/16, 17

[56] References Cited

U.S. PATENT DOCUMENTS

| | | | |
|---|---|---|---|
| 3,030,892 | 4/1962 | Piccardo et al. | |
| 3,478,695 | 11/1969 | Goranson et al. | |
| 3,755,825 | 9/1973 | DeBakey et al. | 623/3 |
| 4,369,530 | 1/1983 | Robinson et al. | 623/3 |
| 4,397,049 | 8/1983 | Robinson et al. | |
| 4,427,470 | 1/1984 | Kolff | 623/3 |
| 4,796,606 | 1/1989 | Mushika | 623/3 |
| 4,820,300 | 4/1989 | Pierce | 623/3 |
| 4,888,011 | 12/1989 | Kung et al. | 623/3 |

FOREIGN PATENT DOCUMENTS

| | | | |
|---|---|---|---|
| 0247015 | 11/1987 | European Pat. Off. | 600/16 |
| 0214295 | 10/1984 | Fed. Rep. of Germany | 623/3 |
| 2591489 | 12/1985 | France | 623/3 |
| 0683755 | 9/1979 | U.S.S.R. | 623/3 |

OTHER PUBLICATIONS

T. Tanaka et al., "Factors Affecting Left-Right Heart Output Differences In Artificial Heart Implanted Animals", 1985, 31 Trans. Am. Soc. Artif. Intern. Organs pp. 211–215.

R. L. Whalen et al., "Volume Compensation For Pulsatile Blood Pumps"; 27 Trans. Am. Soc. Artif. Intern. Organs pp. 110–115; 1981.

*Primary Examiner*—David Isabella
*Assistant Examiner*—Elizabeth M. Burke
*Attorney, Agent, or Firm*—Curtis, Morris & Safford

[57] ABSTRACT

This invention relates to an implantable cardiac prosthesis constituted by a quick-connect, one-piece module comprising two ventricular chambers, rendered biocompatible, independent and activated separately, each being provided with two orifices provided with valves, one of the orifices serving for ejection and the other for inlet of the blood, and with a separate activation and regulation device constituted by an electromechanical member actuating a pair of membranes, characterized in that the first membrane is a mechanical membrane actuated by a piston or a transmission fluid pressurized by means of said electro-mechanical member, and the second membrane, in contact with the blood, is a floating biocompatible membrane, moving under the action of the first membrane between the diastole and systole positions and under the pressure of the blood between the systole and diastole positions.

14 Claims, 3 Drawing Sheets

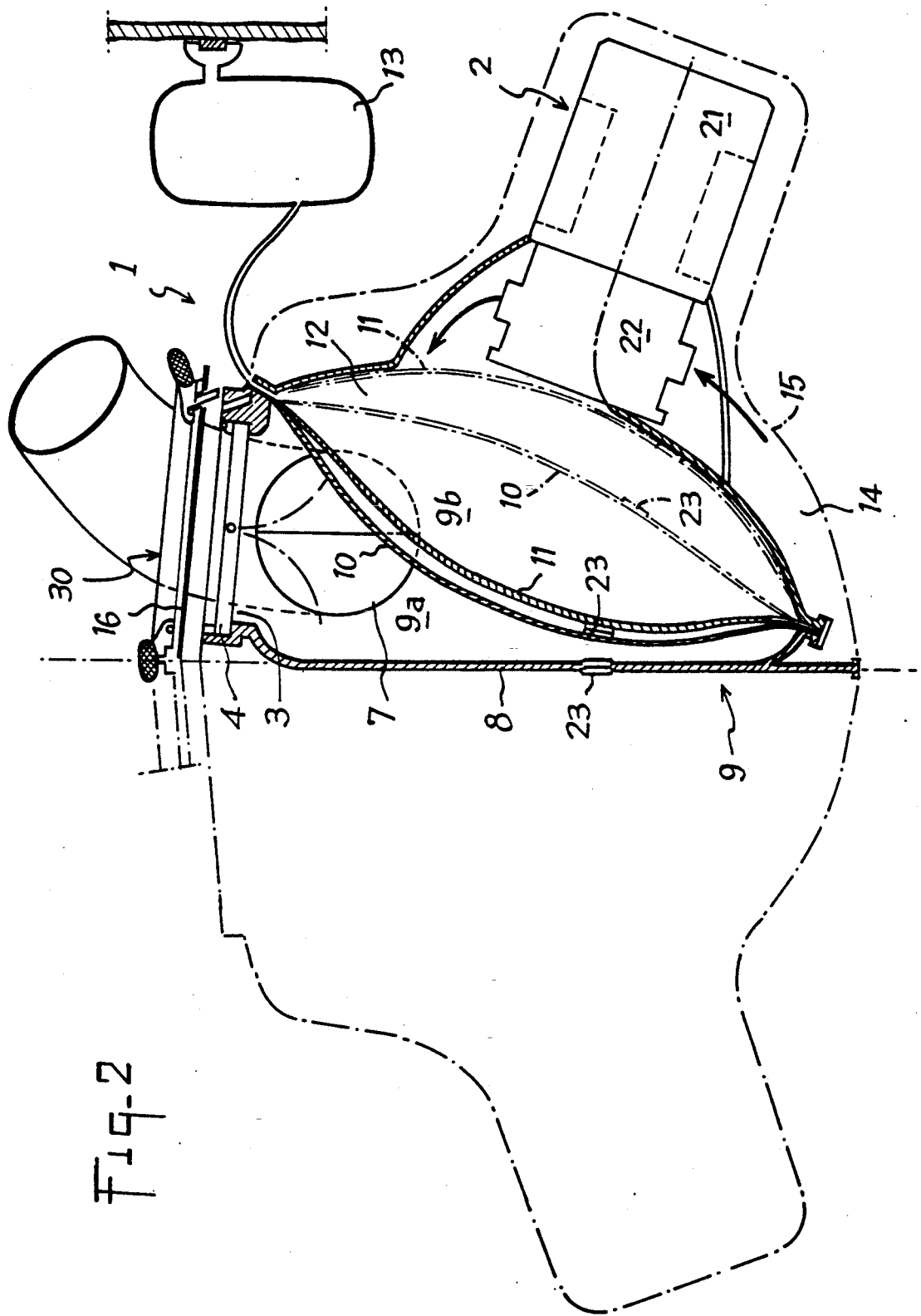

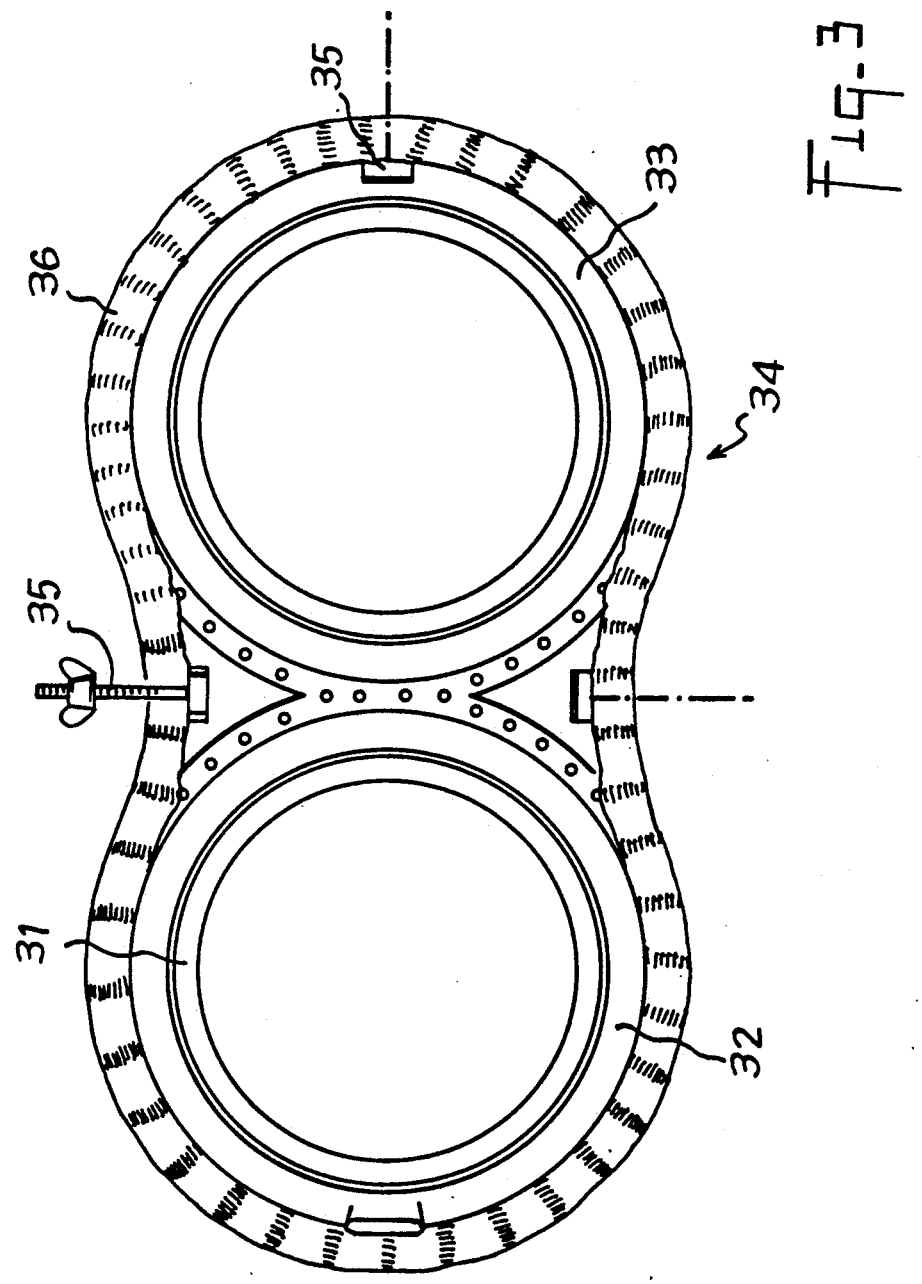

QUICK-CONNECT, TOTALLY IMPLANTABLE CARDIAC PROSTHESIS WITH FLOATING MEMBRANES AND REMOVABLE SENSITIVE ELEMENTS

FIELD OF THE INVENTION

The present invention relates to a quick-connect, totally implantable cardiac prosthesis incorporating floating membranes and removable sensitive elements.

Such a prosthesis is intended for an implantation which is either temporary whilst awaiting a heart transplant, or definitive in patients who cannot benefit from a transplant for medical or other reasons.

BACKGROUND OF THE INVENTION

Such prostheses have already formed the subject matter of several prior inventions, for example the one described in French Application FR 2 446 631.

This prosthesis is essentially constituted by a biventricular one-piece assembly which comprises a tight shell implantable in the pericardiac cavity, made of a material which is compatible and non-toxic with respect to the surrounding tissues and presenting a specific geometry, which reproduces the configuration of the natural heart in two right and left ventricular chambers.

This prosthesis contains: 1) a device for pumping of blood essentially constituted by two membranes, of which one defining the right ventricle works in elongation and of which the second defining the left ventricle works in deformation; 2) valves mounted in the inlet and outlet orifices; 3) means for activating the above-mentioned pumping membranes which furnish them with supply pressures substantially equivalent to the physiological values; 4) means for regulating the cardiac output as a function, on the one hand, of the filling pressure and, on the other hand, of the aortic pressure.

However, with such a prosthesis, a) the activation and regulation means controlling the pumping membranes is not mounted directly on the prosthesis, which increases the volume of the whole and complicates implantation thereof; b) the activation means is unique for the two membranes, rendering the problems of regulation more delicate and random; c) the prosthesis is not rendered biocompatible; and d) it does not allow replacement of certain of its functional elements, which operation may prove necessary in the event of a failure or wear and which it is desirable to be able to effect without changing the whole prosthesis.

U.S. Pat. No. 4,397,049 (ROBINSON et al) describes a cardiac prosthesis comprising two ventricular chambers, each being provided with two orifices, one serving for the inlet of the blood, the other for ejection, and with an activation device constituted by an electro-pneumatic member. However, each chamber presents only one flexible membrane.

Patent FR 2 370 184 (NIKKIOS) describes a pulsatile pump for blood circulation comprising a driving pouch provided with an inlet orifice and with a delivery orifice provided with valves, said pouch being in contact with a pressure transmission chamber defined by a diaphragm and compressed by a piston to generate a movement corresponding to the physiological pulsation. However, this pump is not implantable.

U.S Pat. No. 3,478,695 (GORANSON et al) describes a heart pump with a chamber comprising at least two deformable enclosures, the first being connected to a source of pressure and the other being connected to the heart; pressurization of the first having for its effect to compress the second directly upon contact and thus to provoke delivery of a determined volume of blood towards the heart. The bladder inflates under the effect of the pressurization of the first enclosure and makes it possible to avoid, after delivery, the second enclosure resuming its initial shape too rapidly by suddenly sucking a fresh volume of blood.

However, this pump cannot be mounted directly either on the heart or on any prosthesis.

SUMMARY OF THE INVENTION

The present invention overcomes these drawbacks for the first time and in satisfactory manner by proposing an implantable cardiac prosthesis constituted by a quick-connect, one-piece module comprising two ventricular chambers, rendered biocompatible, completely independent and activated separately, each ventricular chamber being provided with two orifices provided with valves—one of the orifices serving for ejection, the other for inlet of the blood—and with a separate activation and regulation device constituted by an electro-mechanical member and by a pair of membranes, characterized in that the first membrane is a mechanical membrane actuated either by a transmission fluid pressurized by means of said electro-mechanical member, or by a piston animated by a motor in accordance with the so-called pusher plate mode, and the second membrane, in contact with the blood, is a floating biocompatible membrane, moving under the action of the first membrane during systole and under the action of the pressure of the blood during the diastole.

The displacement of the membranes necessitates, on the one hand, a fluid reservoir constituted by a deformable sac enveloping the prosthesis, on the other hand, a compliance chamber connected to the space separating the two membranes. This latter chamber, by its subcutaneous position which is therefore easily accessible by transcutaneous puncture, makes it possible to obtain useful information on the pressures, volumes and possible modifications of the fluid between membranes. It also allows permanent or temporary communication with the open air.

Another feature of the prosthesis of the invention lies in the arrangement of the inlet ducts of the two ventricular chambers which are grouped and connected on the same bezel element, said bezel being removably and rapidly connected to a receptacle of identical shape sutured on the patient's natural atria.

The bezel sutured on the atria and which serves as receptacle for the prosthesis is in one piece and provided with suture devices ensuring tightness. It may be temporarily obturated by an occlusive plate which makes it possible to check the tightness of the receptacle before implanting the prosthesis.

The prosthesis of the invention further comprises, on the wall of the ventricular chambers as well as on each of the membranes, sensors adapted to determine at any instant the position of the floating membrane in order to adjust the flowrate and working frequency of the electro-mechanical member with a view to regulating the stroke of the membranes and the frequency of the beats.

The membranes, electro-mechanical members and valves, elements most sensitive to wear, are removably mounted on the module in order to allow rapid standard replacement thereof.

The originality of the cardiac prosthesis of the invention also resides in the complete separation of the physiological components (e.g. those in contact with blood) from the mechanical components. The part in contact with the blood is constituted by haemocompatible materials and components. The electro-mechanical members are not in contact with the blood, which limits the extent of the engineering compromises which must be made. Another original element is the single-piece design with a separate motive power of the two ventricles so as to facilitate their respective regulation.

The cardiac module proper therefore comprises two independent ventricular chambers having the functions of right ventricle and of left ventricle, four orifices (one inlet duct and one ejection duct for each chamber), four valves (one for each orifice) and two membranes in each chamber.

The electro-mechanical members ensure, for each chamber of the module, actuation of the membranes at a given frequency with a given stroke, thus allowing regulation of the blood outputs by varying the frequency and/or the volumes displaced.

The electro-mechanical pumping members and electronic regulation members are totally isolated from the blood medium. They are miniaturized, mounted on the module in an appendicular arrangement and in the free spaces between the two ventricular chambers. The appendicular arrangement which constitutes an original element of this prosthesis allows their transpericardiac arrangement in the pleural cavities, this considerably reducing the intrapericardiac dimensions and facilitating heat exchanges between the driving members and the lungs.

It is therefore the membranes which constitute the "physical and biological interface" between the blood medium and the electro-mechanical members.

The blood output must be able to be permanently modified as a function of the organism's requirement, either by varying the volume of admission and/or by varying the volume of ejection and/or by varying the frequency.

In the prosthesis according to the invention, the system for regulating output in response to signals from sensors and the hemodynamic status of the organism (e.g. circulatory resistance, compliance, filling pressure and other factors well known to the skilled artisan) is as follows: the "mechanical" membrane is moved by the electro-mechanical or electro-hydraulic actuator between a position of advance (systole) and of withdrawal (diastole). A first element of regulation is constituted by the potential of this membrane to move through all or only part of its stroke both during systole and during diastole. The floating membrane for its part adds a second complementary element of regulation more sensitive than the preceding one. Its diastolic displacement is a function of the pressure and of the filling volume of blood. A third element of regulation is the frequency of displacement of the membranes. These three elements of regulation are put into play either passively or actively as a function of information obtained by different sensors, only one element of which determines the position of the floating membrane.

The sensors are sensors of positioning of the two membranes, sensors of pressure and sensors of partial oxygen pressure, located in the different afferent or efferent cavities or vessels.

The heart is a pulsed output generator and the pressure curves are entirely determined by the force of pulsion on the membranes, the opening/closure of the valves, the haemodynamic conditions of the upstream and downstream networks (compliance pressures). The shape of the pressure curve of the prosthesis according to the invention therefore optimally reproduces the curve of evaluation of the volume delivered as a function of time.

The floating membrane, called biocompatible membrane, which constitutes the interface with the blood is therefore actuated by a second membrane, called mechanical membrane. This latter is itself actuated by a piston of the so-called pusher plate type or preferably by a fluid which allows a better distribution of the mechanical stresses. The pressures generated in the ventricular chambers are generally of the order of 100 to 140 mmHg for the left ventricle and 35 to 40 mmHg for the right ventricle. The so-called transmission fluid is moved by the electro-mechanical member and more particularly by a hydraulic positive displacement micropump itself combined with a brushless D.C. micromotor or autosynchronous motor with sufficient power.

Output may be varied by varying the speed of the motor, the frequency of reversal of direction of the motor, or by changing the volumetric displacement of the pump.

This micromotor is immersed in the transmission liquid and presents electronic controls. The liquid is stored in a reservoir constituted by a deformable, non-elastic, tight envelope surrounding the cardiac module and the electro-mechanical and electronic members.

The hydraulic solution eliminates the problems of mechanical wear of the membranes. The mechanical membrane is not floating and its position depends on the volume delivered by the pump.

The cardiac module also presents sensors of blood pressure, and for assessing filling of each of the ventricles or of the reservoir containing the transmission liquid. The cardiac module also presents sensors for measuring the partial oxygen pressure of the left and right cavities using colorimetric processes.

The electronic control of the autosynchronous motor exploits the position information given by the sensors of the rotor, effects synchronization of the rotary field with the permanent magnet and amplifies the signal delivered to the coils of the stator.

The motor is regulated with a digital electronic card presenting logic integrated circuits which make it possible to reproduce the cardiac cycle by modulating the durations of reversal of direction and by monitoring at each instant the speeds of rotation, the acceleration and the braking.

This card is used with an electronic card for exploiting the signals coming from the sensors of cardiac state and with the electronic microprocessor which monitors and regulates the cardiac output.

The electric motors, the pumps, the electronic elements and the sensors are immersed in the transmission liquid in order to facilitate the heat loads and to reduce noise.

BRIEF DESCRIPTION OF THE DRAWINGS

The invention will be more readily understood on reading the following description with reference to the accompanying drawings, in which:

FIG. 2 is a view thereof in transverse section representing the systolic and diastolic positions of the floating membrane.

FIG. 3 is a plane view from above of the receptacle on which is removably connected the inlet bezel of the module.

DETAILED DESCRIPTION OF THE DRAWINGS

Figure 1:
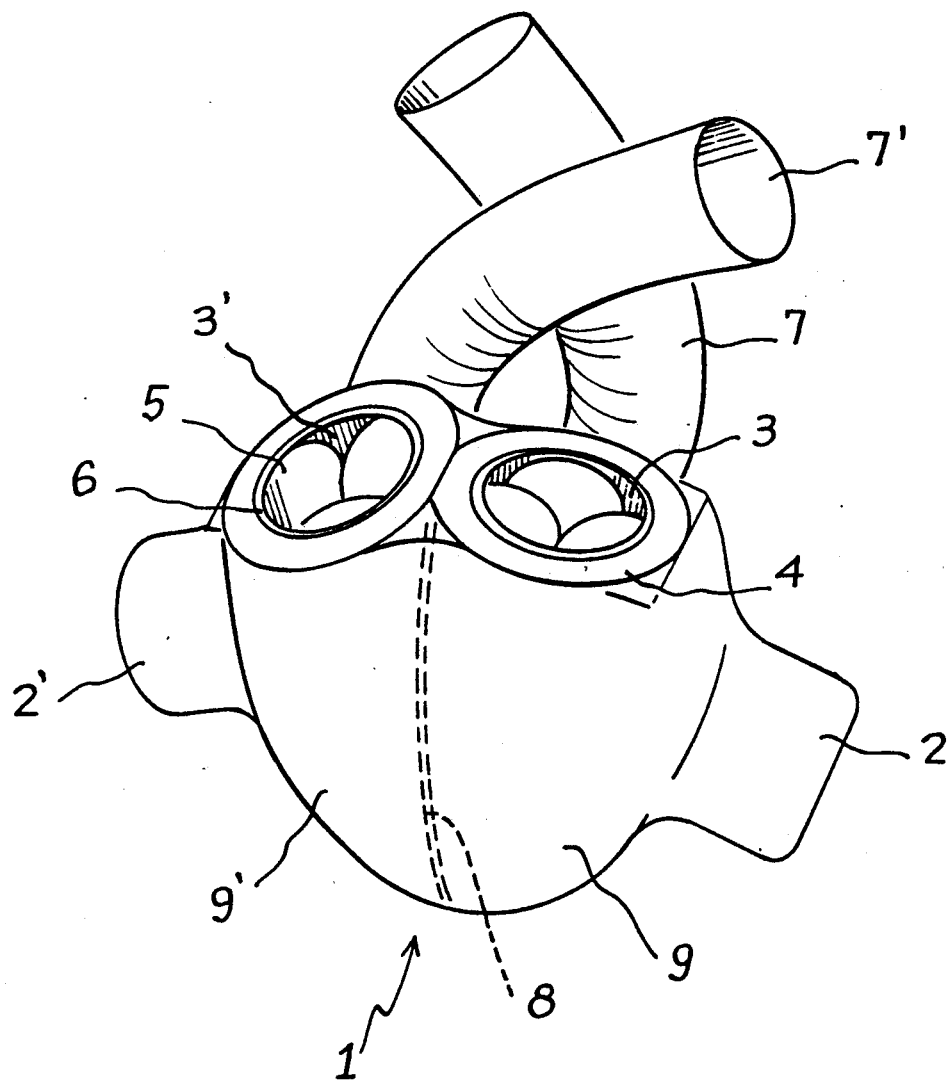
FIG. 1 shows an overall view of the cardiac prosthesis according to the invention.

FIG. 1 is an overall view of the cardiac prosthesis according to the invention.

This Figure shows the appendicular arrangement of the electro-mechanical members 2, 2' on the module 1.

The two inlet ducts 3, 3' grouped side by side on one single bezel 4 are provided with admission valves 5 and with a seal element 6. The bezel is adapted to be quickly and easily connected to a receptacle 30 (not shown in this Figure) sutured on the patient's natural atria. The two ejection ducts 7, 7' are independent and are provided with ejection valves 5' (not shown in this Figure). These ducts are sutured directly on the arteries. Wall 8 completely isolates ventricle 9.

FIG. 2 is a transverse half-section of the prosthesis of the invention. In this Figure, only the left heart constituted by the left ventricle 9 has been shown, wall 8 completely isolating it from the right ventricle 9'.

Ventricle 9 is divided into two parts: a biological chamber 9a and a mechanical chamber 9b, the interface between these two chambers being constituted by a mobile biocompatible membrane 10. It is therefore the position of this membrane 10 which determines the volume of the biocompatible chamber 9a and consequently the quantity of blood admitted or ejected. The membrane 10 is floating, i.e. mobile unilaterally between the systolic position corresponding to the . end of the period of ejection, moment when the biocompatible chamber 9a has a minimum volume, and the diastolic position corresponding to the end of the period of admission, moment when the biocompatible chamber 9a has a maximum volume (of the order of 60 to 80 cc), depending on the size of the prosthesis.

The membrane 10 is actuated by a second, so-called mechanical membrane 11. During the phase of ejection, the membrane 11 pushes membrane 10 from the diastolic position to the systolic position, then, during the inlet phase, the membrane 10 returns to the diastolic position under the simple effect of the blood pressure.

The diastolic position of the membrane 10 corresponds to an equilibrium on either side of said membrane between the filling blood pressure (which is of the order of 10 mmHg for the left heart and 8 mmHg for the right heart ) and the compliance chamber.

Between the biocompatible membrane 10 and the mechanical membrane 11 there exists an intermediate free volume 12 occupied by a fluid maintained during diastole at a pressure slightly less than or equal to the pressure of filling of the right heart or of the left heart. This free volume 12 is in communication with a compliance chamber 13 easily accessible from outside the body in order to be able, if necessary, to readjust the pressure of intermediate free volume.

The mechanical membrane 11 is itself actuated by means of an electro-mechanical member 2 via a transmission fluid 14 (and preferably a liquid) stored in the reservoir constituted by a tight deformable envelope 15 surrounding the module 1, the electro-mechanical members 2, 2" and the regulation elements. This arrangement makes it possible to reduce the noise of the mechanical elements and promotes heat exchanges.

The electro-mechanical member 2 is therefore immersed in said transmission fluid and is composed of of an electric micromotor 21 combined in the case of the Figure with a hydraulic micropump 22. The micromotor 21 may for example be an autosynchronous motor. During the phase of ejection, the micropump 22 sucks the liquid 14 directly in the reservoir 15 and delivers it in a very short time against the mechanic membrane 11 to push it in contact with the biocompatible membrane 10. During the phase of admission, the micropump 22 sucks the liquid 14 previously in contact with the membrane 11 to reservoir 15, which causes the membrane 11 return to its position of rest. The frequency of the heart beat therefore corresponds to the frequency of reversal of the direction of rotation of the micropump 22. The stroke of the membrane 10 depends on the stroke of the membrane 11 and therefore on the volume of liquid 14 delivered by the micropump 22 as well as on the ventricular filling pressure. The micromotor 21 and the micropump 22 are controlled by an electronic monitoring and regulation device comprising a set of analog sensors 23 mounted in particular on the wall 8 and on the membranes 10, 11 in order to continuously monitor the position of the membranes, the frequency of the beats, the blood pressure inside the ventricular chamber and the compliance chamber, the pressure of the transmission liquid, the partial oxygen pressure, etc. . . The information furnished by the sensors 23 is used by the electronic monitoring device to automatically modify or adjust the operational parameters of the module 1 to predetermined values.

The ventricle 9, with reference to FIGS. 2 and 3, presents two orifices, one serving as inlet duct 3 and the other as ejection duct 7. These orifices are respectively provided with an inlet valve 5 and an ejection valve 5' and cause the ventricle 9 to communicate with the rest of the circulatory system. The ejection duct 7 is adapted to be sutured directly on an artery.

The inlet ducts 3, 3' of ventricles 9, 9' are grouped and connected on the same bezel 4.

The bezel 4 itself is removably and quickly connected on the receptacle 30 sutured on the patient's natural atria.

All the fragile elements or those likely to wear out quickly, such as the valves, micromotors, micropumps and membranes, are removably mounted on the module in order to be replaced easily without changing all the module 1.

The receptacle 30 is constituted by a bezel 34 symmetrical to the bezel 4 and on which the module 1 is removably and quickly connected. Its originality comes from the fact that it is in one piece connecting the two admission orifices 32, 33. It comprises a suture element constituted for example by a peripheral suture ring 36 made of fabric DACRON (registered trademark), a polyester fiber made by DUPONT completed by an inter-orifice fastening tape of the same fabric. The inter-orifice fastening tape comprises regularly spaced apart perforations 38 for the passage of the suture threads and a notch covered by the suture ring 36 except between the two orifices 32, 33. The notch 37 is adapted to house the knots of the suture threads in order to ensure perfect joinder between the receptacle and the prosthesis. This receptacle 30 may be occluded by a plate 16 (cf. FIG. 2) to check the tightness of the sutures. It presents seals with the prosthesis and the quick-connect elements 35.

What is claimed is:

1. An implantable cardiac prosthesis comprising a quick-connect, one-piece module, said prosthesis comprising two biocompatible ventricular chambers, said chambers being independent and being able to be separately activated, and each having two orifices with valves, one of said orifices serving as a blood ejection duct and the other as a blood inlet duct, and said prosthesis further having separate activation and regulation means, said means comprising an electro-mechanical member whose output and working frequency are controlled to activate first and second membranes so as to regulate their stroke and frequency of beat, said first membrane comprising a mechanical membrane comprised of a first material, said first membrane being actuated by a transmission fluid pressurized by means of said electro-mechanical member, and said second membrane, which is in contact with blood, comprising a floating biocompatible membrane comprised of a second material, said first and second membranes being separated in diastolic position by a compliance fluid whereby said second membrane is movable by said first membrane between the diastole and systole positions and further movable by blood pressure from the systole to the diastole position, said prosthesis further comprising a bezel and a receptacle, said inlet ducts of the two ventricular chambers being grouped on the same bezel and being connected to said receptacle situated on the patient's natural atria; and, said first material being different from said second material.

2. The cardiac prosthesis of claim 1, wherein said receptacle comprises two admission orifices and suture elements, said orifices being grouped and connected on the same bezel for connection with both the atria and the prosthesis by suture elements composed of a synthetic fabric.

3. The suture elements of claim 2, wherein said synthetic fabric is composed of polyester fibers.

4. The cardiac prosthesis of claim 2, wherein said suture elements comprise a peripheral ring and said cardiac prosthesis has an inter-orifice fastening tape comprising regularly spaced apart perforations for passage of suture threads and a notch to house knots of the suture threads to ensure perfect joinder between the receptacle and the prosthesis.

5. The cardiac prosthesis of claim 4, which further comprises a plate for occluding the admission orifices which may be fixed thereto in order to check tightness of the suture threads before effecting connection with the prosthesis.

6. The cardiac prosthesis of claim 1, wherein said first and second membranes define therebetween in diastolic position an enclosure occupied by said compliance fluid and communicating with a compliance chamber, the volume of said enclosure being a function of a filling pressure of the ventricular chamber.

7. The cardiac prosthesis of claim 6, wherein the compliance chamber comprises external filling means subjected to atmospheric pressure.

8. The cardiac prosthesis of claim 6, wherein said enclosure further comprises a deformable, non-elastic tight envelope laterally surrounding the module, the electro-mechanical member and an electronic monitoring device.

9. The cardiac prosthesis of claim 1, further comprising on a wall of the ventricular chambers as well as on each of said first and second membranes, sensors to determine any position of said second membrane in order to adjust the output and working frequency of the electro-mechanical member in order to regulate the stroke of said first and second membranes and the frequency of the beat.

10. The cardiac prosthesis of claim 9, wherein said sensors are operatively connected to an electronic monitoring device able to automatically adjust the output and working frequency of the electro-mechanical member to predetermined values.

11. The cardiac prosthesis of claim 1, wherein the electromechanical member comprises an electric micromotor coupled with a positive displacement micropump having an adjustable output and a gear.

12. The cardia prosthesis of claim 11, wherein said electric micromotor, an electronic monitoring device and sensors are immersed in the transmission fluid in order to carry away heat and to reduce noise.

13. The cardiac prosthesis of claim 12, further comprising sensors for providing information bout any position of said first and second membranes, sensors for providing information about blood pressure, sensors for providing information about transmission fluid pressure, and sensors for providing information about blood partial oxygen pressure operatively connected to an electronic monitoring device above to automatically adjust the output and working frequency of said electric micromotor to predetermined values.

14. The cardiac prosthesis of claim 1 wherein said first and second membranes, the electro-mechanical members and the valves are removably mounted on the module in order to allow rapid filling thereof.

* * * * *